United States Patent [19]
North, Jr.

[11] Patent Number: 5,971,713
[45] Date of Patent: Oct. 26, 1999

[54] PULSELESS LIQUID DELIVERY SYSTEM USING A PULSATILE PUMP

[76] Inventor: Howard L. North, Jr., 100 Via Santa Maria, Los Gatos, Calif. 95030-6334

[21] Appl. No.: 09/222,057

[22] Filed: Dec. 29, 1998

Related U.S. Application Data

[62] Division of application No. 08/779,505, Jan. 7, 1997, Pat. No. 5,915,925.

[51] Int. Cl.$^6$ ..................................................... F04B 49/06
[52] U.S. Cl. ............................ 417/36; 417/32; 417/44.9; 73/149; 73/209 R
[58] Field of Search ................................. 417/32, 36, 37, 417/44.9, 63; 73/149, 290 R, 168

[56] References Cited

U.S. PATENT DOCUMENTS

| 3,349,785 | 10/1967 | Duffy | 137/30 |
|---|---|---|---|
| 3,738,776 | 6/1973 | Debare | 417/38 |
| 3,937,596 | 2/1976 | Braidwood | 417/36 |
| 3,958,898 | 5/1976 | Abrahams et al. | 417/36 |
| 4,278,403 | 7/1981 | Shaefer | 417/38 X |
| 4,738,595 | 4/1988 | Gaiser | 417/36 |
| 5,213,477 | 5/1993 | Watanabe et al. | 417/20 |
| 5,315,867 | 5/1994 | Hartel et al. | 73/149 |
| 5,385,069 | 1/1995 | Johnson, Jr. | 73/571 |
| 5,425,624 | 6/1995 | Williams | 417/36 |
| 5,777,221 | 7/1998 | Murthy et al. | 73/149 |

*Primary Examiner*—Timothy S. Thorpe
*Assistant Examiner*—Ehud Gartenberg

[57] ABSTRACT

A liquid supply system including a diaphragm pump, a novel liquid accumulator providing exceptionally high volume compliance, and a control of accumulator volume within narrow limits by continuous control of the pump motor. The accumulator achieves high volume compliance by arranging the kinematics of a main spring loading the accumulator to have a negative spring rate equal to the sum of all other positive spring rates produced by a second spring used to adjust the accumulator pressure, by the diaphragm, and by a pivot for a sensor lever. This lever moves with the diaphragm to actuate an optical sensor producing an signal indicative of small changes in liquid volume in the accumulator. This signal continuously modulates the power to the motor driving the pump so as to maintain the accumulator volume lose to a datum valve. This close control of liquid volume in a high compliance accumulator provides substantially pulse-free constant pressure liquid delivery from a pulsatile pump. The second spring may be adjusted to modify this constant pressure without disturbing the balance between positive and negative spring rates. Adjustment may be automatic in response to a variable such as liquid temperature whereby liquid pressure is automatically increased with lower liquid temperature to maintain liquid flow substantially constant through a flow cytometry apparatus used for particle analysis.

16 Claims, 4 Drawing Sheets

PULSELESS LIQUID DELIVERY SYSTEM USING A PULSATILE PUMP

This is a division of Ser. No. 08/779,505, filed Jan. 7, 1997, now U.S. Pat. No. 5,915,925.

BACKGROUND—FIELD OF INVENTION

This invention relates to a system for delivery pressurized liquid to an apparatus, such as a flow cytometer, and in particular to a system having an improved liquid accumulator/pump control means for providing continuous modulation of power to a liquid pump drive means.

BACKGROUND—DESCRIPTION OF RELATED ART

Flow cytometry apparatus has commonly used a liquid suspension of particles ensheathed by a particle-free liquid wherein this coaxial flow passed through an analysis region and thence often to a particle sorting means. Such coaxial flow systems are shown in an article by P. J. Crossland-Taylor, Nature 171, 37 (1953) and in U.S. Pat. No. 3,826,364, which are hereby referred to and incorporated herein. Sheath liquid is usually a phosphate buffered saline solution and is usually supplied to the analysis region from a closed reservoir pressurized by air from an air pressure regulator connected to a source of air at a higher pressure (note items 16, 26, and 22 of U.S. Pat. No. 3,826,364). Since particle analyzers and particle sorters often depend on consistent liquid flow velocities through the analysis region, this air pressurized sheath supply system has the following shortcomings:

1) As the sheath supply reservoir empties during operation of the flow cytometer the liquid level decreases and the loss of head causes a decrease in liquid flow rate;
2) Changes in sheath liquid temperature cause changes in sheath liquid flow rate due to changes in liquid viscosity. Changes in liquid temperature can result from changing ambient air temperature or from sheath reservoir replenishment with liquid at a different temperature.
3) Replenishment of sheath liquid is inconvenient, requiring stopping operation of the flow cytometer, de-pressurizing the reservoir, opening and refilling the reservoir, re-pressurizing the reservoir and restarting the flow cytometer;
4) The pressurized reservoir has often been a stainless steel ASME pressure vessel which is both expensive and unsuitable for visual observation of liquid level in the reservoir;
5) Air dissolves in the sheath liquid in time and can later be released as bubbles as the liquid loses pressure while flowing through filters, valves, and conduits to the analysis and sorting regions. Bubbles in these regions often prevent proper analysis or sorting functions; and
6) When pressurized air supply is not available at a flow cytometer installation, then a separate air compressor, motor, reservoir, and controls must be provided.

Attempts to use gear or centrifugal pumps to pressurize sheath liquid, usually phosphate buffered saline, have not produced practical designs. Neither pump is inherently self-priming so initial start up or restart after running out of liquid requires the operator to perform special procedures such as bleeding air from the system. If either pump is kept running when liquid flow through the flow cytometer stops, then the pump will tend to overheat and be damaged. Solutions such as an overflow/overpressure line for returning pressurized liquid back to the supply reservoir or stopping the pump add cost and complexity. Also gear and centrifugal pumps suitable for long life operating with corrosive saline are expensive.

Many of these shortcomings of gear or centrifugal pumps are avoided by diaphragm pumps, particularly those with polymer housing and with elastomer diaphragms and check valves. However, diaphragm pumps require a liquid accumulator to supply pressurized liquid during the refilling stroke of the pump. Common accumulators employ a piston loaded by a spring or a bladder loaded by compressed gas or combinations thereof (as is shown in U.S. Pat. No. 4,278,403. This patent shows an accumulator 35 which operates a pump P via a switch 43 in an on/off mode from a pressure movable partition element, piston 36. This on/off mode of pump control with its dead band between On and Off conditions results in significant changes in pressure in accumulator 35. In addition the friction from seals for piston 36 and stem 41 produce inaccuracies in the sensing of pressure in accumulator 35. Also these seals are subject to wear and leakage which limit the durability of accumulator 35.

OBJECTS AND ADVANTAGES

Accordingly several objects and advantages of my invention are:

a) to provide essentially pulse-free constant pressure liquid to an apparatus, such as a flow cytometer, unaffected by liquid level changes in the supply reservoir;
b) to employ an unpressurized supply reservoir which is easy to refill, is simple and low cost, may be raised and lowered without affecting the liquid supply pressure, does not introduce air into the sheath liquid, does not require a separate air supply and valves, may be sized large to reduce replenishment frequency, may be transparent for visual observation of liquid level, and may be replenished without stopping operation of the apparatus;
c) to provide for manual or automatic adjustment of the sheath liquid pressure as required to compensate for variations in sheath liquid temperature and thereby maintain sheath liquid flow rate substantially constant and thus maintain critical flow cytometer timing such as:
   Particle transit time from laser beam to drop break-off for drop-in-air sorters,
   Particle transit time from laser beam to catcher tube for a catcher tube sorter,
   Particle transit time between laser beams in a multiple laser analyzer or sorter;
d) to provide a novel liquid accumulator which can accept the liquid volume delivered by one stroke of a diaphragm pump with negligible change in liquid pressure; and
e) to provide a self-priming pump in a liquid supply system where the liquid contacts only non-metal parts thus avoiding metal corrosion and contamination of the liquid.

Other objects and advantages are to provide apparatus and method for delivering pressurized liquid to an apparatus which is small, simple, low cost, reliable, durable, quiet, accurate, essentially pulse-free, and which operates with low electric power.

SUMMARY OF THE INVENTION

The present invention is directed to a pulse-free, constant pressure liquid delivery system which may be adapted for connection to an apparatus, such as a flow cytometer. Preferred embodiments of the invention provide for manual or automatic adjustment of the liquid pressure to compensate for variations in liquid supply temperature and thus maintain constant liquid flow rate through the apparatus. This invention avoids many of the problems, inconveniences, and cost associated with other liquid supply systems by use of a novel liquid accumulator design and an electric motor driven reciprocating diaphragm pump controlled by a simple electronic control responsive to the liquid volume in the accumulator.

BRIEF DESCRIPTION OF THE DRAWINGS

The invention may be understood, and further advantages and uses are more readily apparent, when considered in view of the following detailed description of the exemplary embodiments, taken with the accompanying drawings, in which.

DESCRIPTION OF THE PREFERRED EMBODIMENTS

Figure 1:
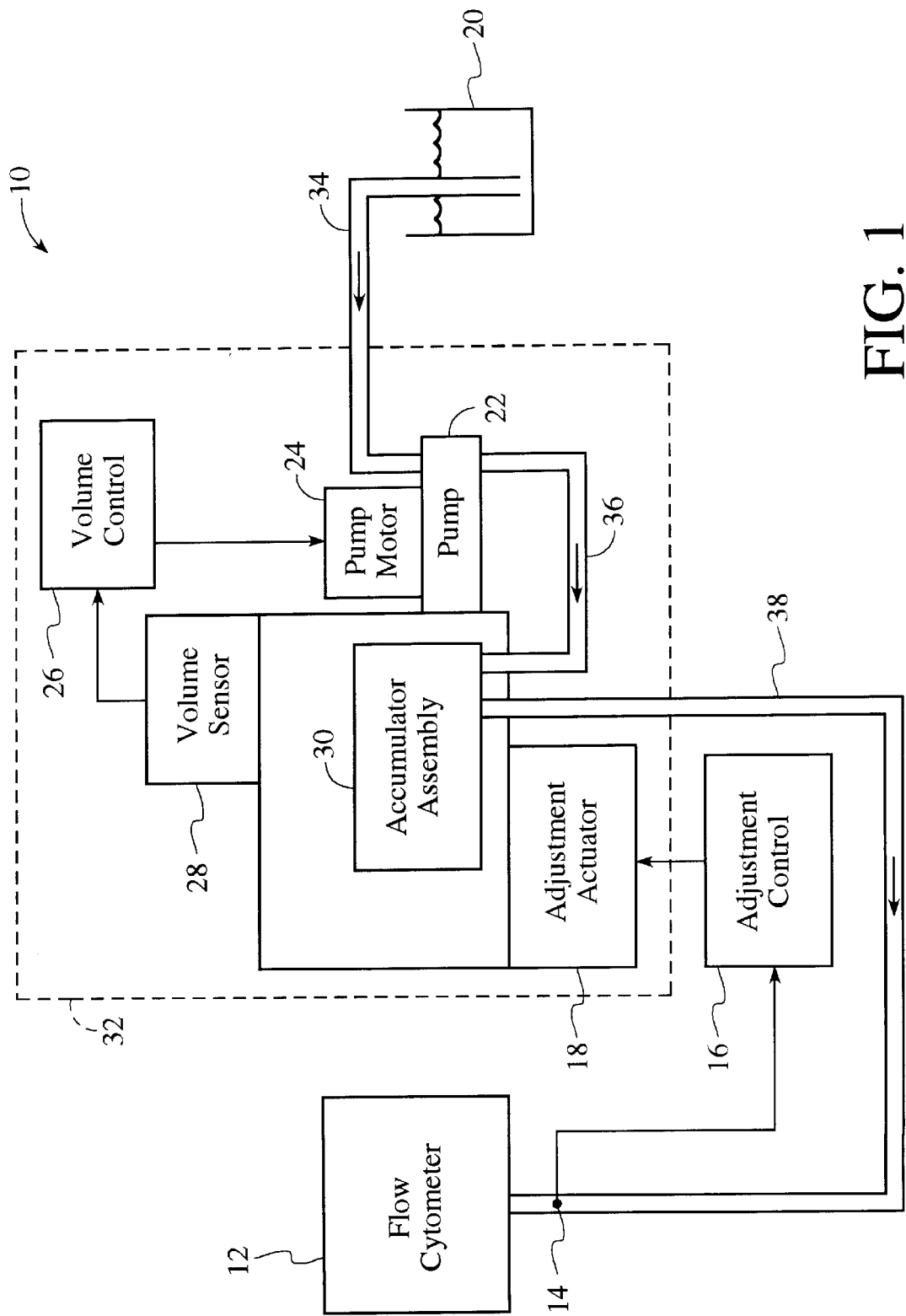
FIG. 1 is a simplified schematic diagram of the liquid supply system as connected to a flow cytometer.

Referring now to the drawings and to FIG. 1 in particular, there is shown a simplified schematic diagram of liquid supply system 10 supplying flow cytometer 12 with a constant liquid flow, all constructed according to the teachings of the invention. Liquid supply system 10 includes reservoir 20 connected via conduit 34 to pump 22. thence via conduit 36 to accumulator assembly 30, thence via conduit 38 to the inlet of flow cytometer 12. Accumulator assembly 30 is part of liquid supply control means 32 for supplying a constant flow of liquid to flow cytometer 12 which includes pump 22, pump motor 24, volume sensor 28, volume control 26, and adjustment actuator 18. Liquid supply system 10 further includes adjustment control 16 connected to liquid temperature sensor 14 and adjustment actuator 18.

Figure 2:
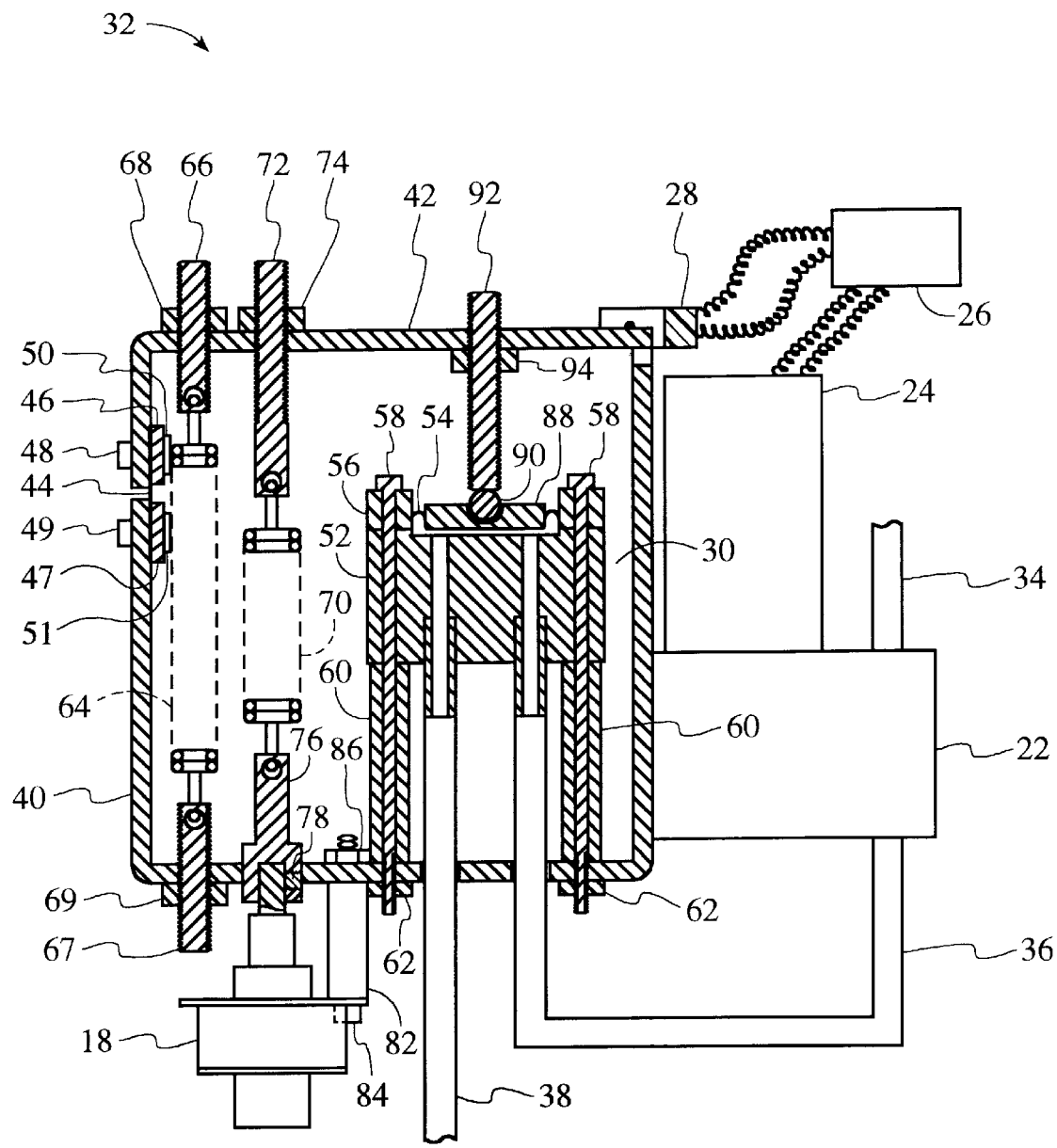
FIG. 2 is a cross-sectional view of the liquid supply assembly taken along the line 2—2 of FIG. 3.

Referring now to FIG. 2 there is shown a cross-sectional view (taken along the line 2—2 of FIG. 3) through the middle of liquid supply assembly 32 which shows accumulator assembly 30 including diaphragm 54 clamped between diaphragm retainer 56 and accumulator body 52 by screws 58, spacers 60, main support 40, and nuts 62. Diaphragm 54 is of the constant area rolling diaphragm type such as for example are manufactured by Bellofram Corporation. Diaphragm 54 is connected via piston 88, ball 90, diaphragm screw 92, and nut 94 to sensor lever 42. Sensor lever 42 is pivotably supported by flexure pivot 44 clamped to sensor lever 42 by flexure retainer 46, two screws 48, and two nuts 50 and is clamped to main support 40 by flexure retainer 47, two screws 49, and two nuts 51. A main spring 64 is attached to sensor lever 42 by main spring support screw 66 and nut 68 and is attached to main support 40 by main spring support screw 67 and nut 69. Main spring 64 is a helical extension spring with a hook at each end for insertion in a hole in spring support screws 66 and 67. An adjustment spring 70 is attached to sensor lever 42 by adjustment spring support screw 72 and nut 74 and to adjustment actuator 18 by coupling 76 and set screw 78. Adjustment spring 70 is a helical extension spring with a hook at each end for insertion in a hole in spring support screw 72 and in coupling 76. Adjustment actuator 18 is fastened to main support 40 by two spacers 82, two screws 84 and tow nuts 86. The adjustment actuator 18 may be, for instance, a stepper motor driven linear actuator such as manufactured by Haydon Switch and Instrument and sold as Model No. 26541 which has 0.001 inch motion per electrical steo. Pump 22 and pump motor 24 may be an integrated assembly such as is manufactured by KNF Neuberger as Model No. NF30KVDC or NF1.30KVDC which are rated for continuous pumping at pressures up to 15 and 85 psi respectively. Pump motor 24 and volume sensor 28 are connected electrically to volume control 26. Pump 22 with pump motor 24 may be mounted on the main support 40 or elsewhere. Liquid supply assembly 32 is preferably oriented so air is naturally purged from accumulator assembly 30 and pump 22 when liquid flows through these components during start up.

Figure 3:
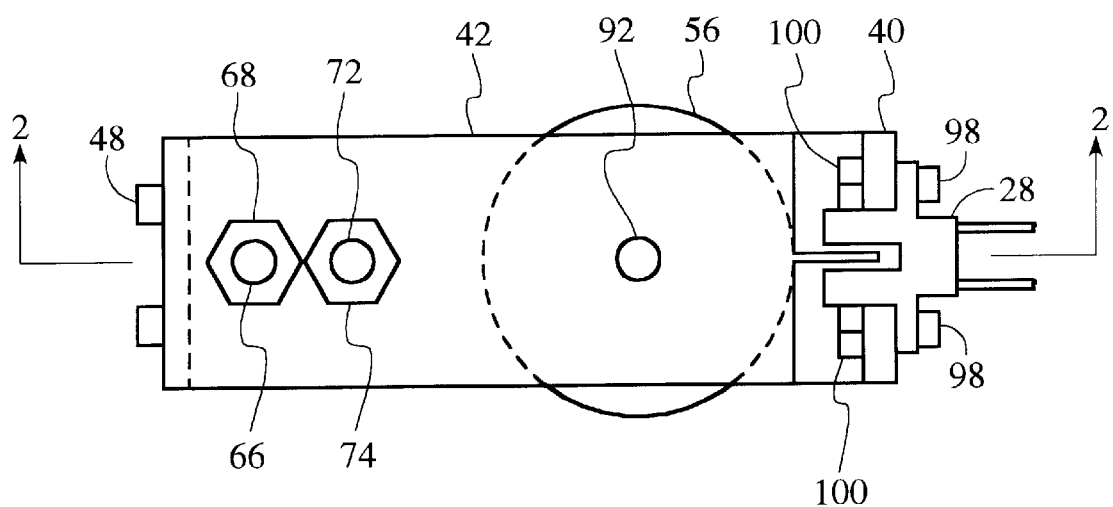
FIG. 3 is a plan view of the volume sensor.

Referring now to FIG. 3 there is shown a plan view of sensor lever 42 and volume sensor 28 which is fastened to main support 40 by screws 98 and two nuts 100. Volume sensor 28 comprises an infrared light emitting diode facing an NPN silicon phototransitor encased in a black thermoplastic housing such as for example is manufactured and sold by Honeywell as Model No. H0A0890-T51. The reduced width end of sensor lever 42 is located within a slot between the light emitting diode and the photo-transistor.

Figure 4:
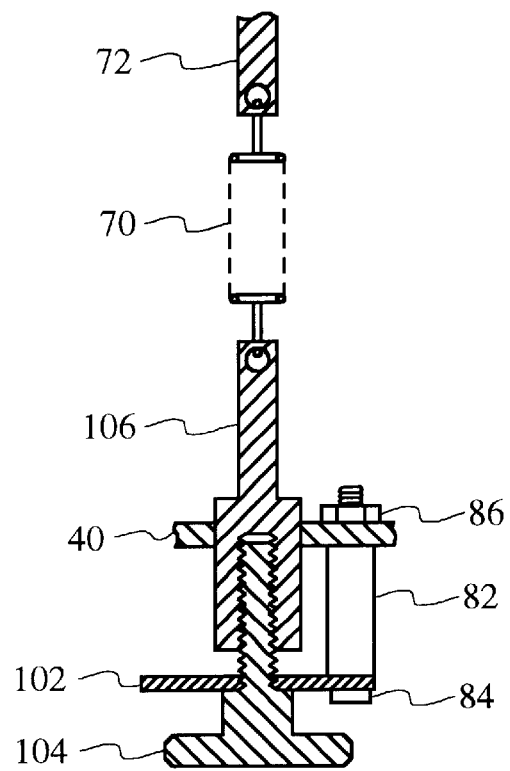
FIG. 4 is a cross-sectional view of the manual pressure adjustment.

Referring now to FIG. 4, there is shown a cross-sectional view of the manual pressure adjustment where the adjustment actuator 18, coupling 76, and set screw 78 have been replaced by support plate 102, and manual adjustment 104 which is threadably engaged with manual adjustment coupling 106 which has a square cross-section slidably engaged with main support 40 in a square hole to prevent rotation of manual adjustment coupling 106.

Figure 5:
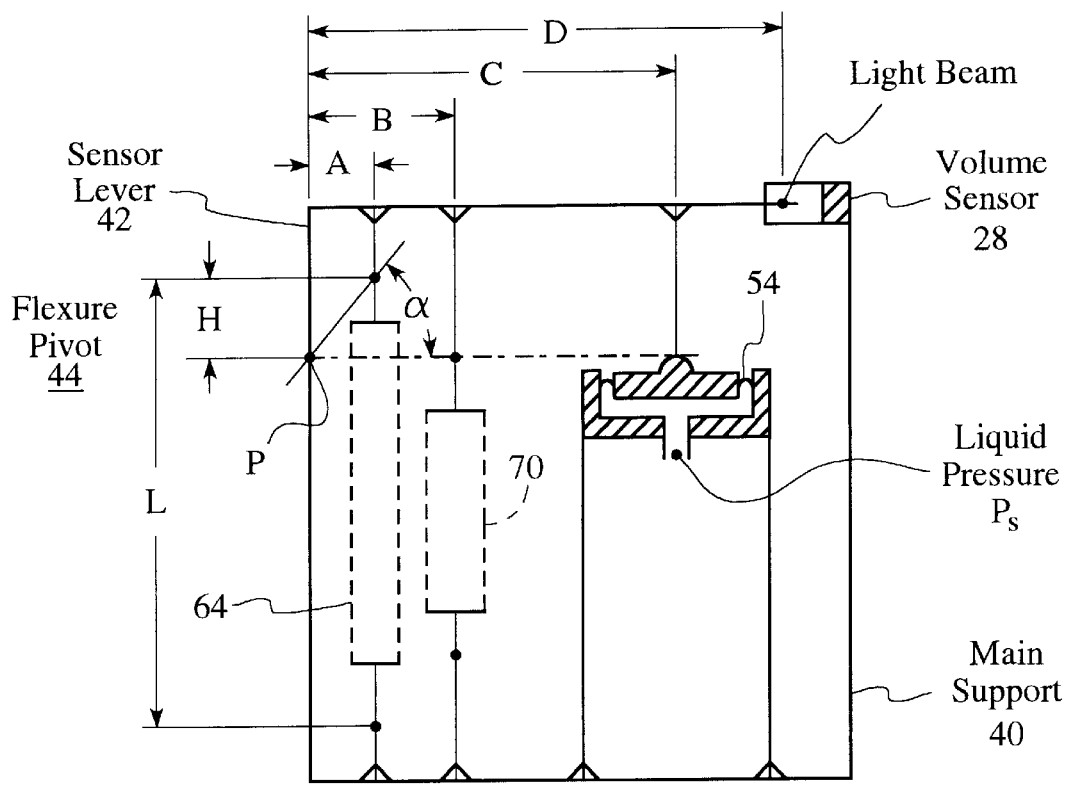
FIG. 5 is a diagram of the kinematic features of the invention.

Referring now to FIG. 5 there is shown a diagram of the essential kinematic features of the invention provided to facilitate explanation of the design of an accumulator having substantially infinite volume compliance. Volume compliance is defined as a small change in accumulator volume divided by the resulting change in accumulator pressure. A,B,C&D are dimensions from the flexure pivot 44 pivot point P to the centerlines for the forces from main spring 64, adjustment spring 70, diaphragm 54, and the light beam of volume sensor 28 respectively. H is the height above pivot point P of the contact of main spring 64 with main spring support screw 66. a is the angle defined by tan a=H/A. L is the installed length of main spring 64 between contacts with main spring support screws 66 and 67. The following terms are defined here:

$K_M$ is the spring rate of main spring 64—lbs./inch $K_A$ is the spring rate of adjustment spring 70—lbs./inch $K_D$ is the spring rate of diaphragm 54—lbs./inch $T_P$ is the torsional spring rate of flexure pivot 44 as installed, in inch lbs./radian. defined as the rate of change in moment about pivot point P per radian change in angle a due to motion of sensor lever 42 about pivot point P $A_D$ is the effective area of diaphragm 54 exposed to liquid pressure—square inches $P_s$ is the liquid pressure acting on the diaphragm—psi $F_M$ is the tension force of main spring 64—lbs.
$F_A$ is the tension force of adjustment spring—lbs.

Accumulator Compliance (cubic inch/psi)
$$= \frac{A_D^2}{K_D + K_A \frac{B^2}{C^2} + \frac{T_p}{C^2} + K_M \frac{A^2}{C^2} - F_M \frac{(L-H)}{L} \frac{H}{C^2}}$$

Figure 6:
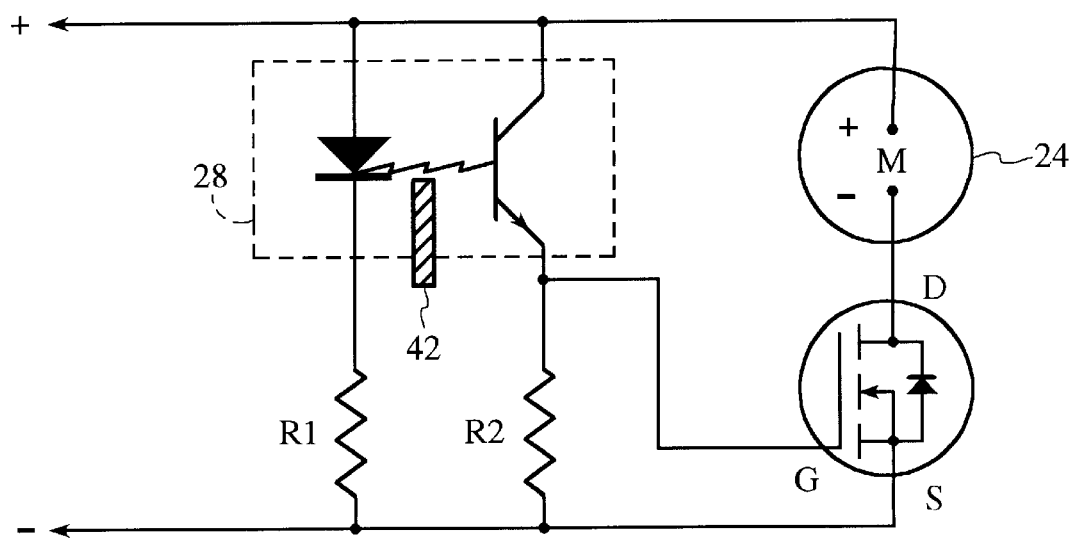
FIG. 6 is an electrical diagram of the volume sensor, volume control, and pump motor.

Referring now to FIG. 6 there is shown a typical volume control 26 used with volume sensor 28 and pump motor 24. Typical components are IRF520 N channel MOSFET, $R_1$=560 ohm and $R_2$=470,000 ohm.

Referring again now to FIG. 1, in operation there will be liquid flow from the supply reservoir 20 through conduit 34 to pump 22 and then through conduit 36 to accumulator assembly 30 and then through conduit 38 to flow cytometer 12. Pump 22 is driven by pump motor 24 which is controlled by volume control 26 which is responsive to volume sensor 28. Referring now to FIG. 2, there is shown that as less liquid is contained in accumulator assembly 30 diaphregm 54 and piston 88 move towards accumulator body 52. In turn ball 90, diaphragm screw 92, nut 94, and sensor lever 42 also move towards accumulator body 52. Sensor lever 42 then moves to permit more light from the light emitting diode to reach the phototransitor in volume sensor 28 which increases the phototransitor conductivity. As shown on and now referring to FIG. 6, this increases the voltage between the gate G and the source S of the MOSFET which increases the current through pump motor 24 driving pump 22. Pump 22 then increases its discharge of liquid into accumulator assembly 30 which causes diaphragm 54, piston 88, ball 90, diaphragm screw 92, nut 94, and sensor lever 42 to move away from accumulator body 52. This motion of sensor lever 42 reduces the light from the light emitting diode reaching the phototransitor in volume sensor 28 which reduces its conductivity. This decreases the voltage between the gate and the source of the MOSFET which reduces the current (and the torque) through the pump motor 24 driving pump 22. Pump 22 then slows down or stops delivering liquid to accumulator assembly 70. In this manner, balance is obtained in this closed-loop control system. This balance is obtained both statically and dynamically throughout the delivery stroke of pump 22 from bottom dead center to near top dead center. However, near the top dead center the control loop tends to become unstable and a small fraction of the stroke volume of pump 22 is delivered to accumulator assembly 30 whether needed or not needed. This fraction is typically less than 10% of the stroke volume of pump 22. After passing top dead center, pump 22 refills from reservoir 20 and returns to bottom dead center rapidly for continued control of liquid volume within accumulator assembly 30.

It is clear that accumulator assembly 30 will have small but significant volume changes during each delivery cycle of pump 22. The liquid supply assembly 32 is provided with a novel kinematic design so that supply pressure $P_s$ within accumulator assembly 30 is essentially unaffected by these small liquid volume changes whereby $P_S$ is fixed within less than + or −0.1% fluctuation during continued operation of pump 22. This accumulator function is produced by arranging the main spring 64 kinematically to produce a negative spring rate at diaphragm 54 which numerically equals the positive spring rate at diaphragm 54 produced by the sum of the spring rates of diaphragm 54, adjustment spring 70 and flexure pivot 44. Referring now to FIG. 5 the negative spring rate effect of main spring 64 is produced by making H large enough in relation to the other parameters that as sensor lever 42 moves to increase angle a, the fractional decrease in moment arm from main spring force to pivot P is greater than the fractional increase in force from the main spring due to its greater extension. The net effective spring rate, $K_e$, at the diaphragm centerline is given by:

$$K_e = K_D + K_A \frac{B^2}{C^2} + \frac{T_p}{C^2} + K_M \frac{A^2}{C^2} - F_M \frac{(L-H)}{L} \frac{H}{C^2} - \text{lb/in.} \quad \text{Eq. 1}$$

$$\text{where } T_p = \frac{Ewt^3}{12h} - \text{inch lbs./radian} \quad \text{Eq. 2}$$

where for pivot support 44:
E=Young=s modulus of elasticity—psi
w=width—inches
t=thickness—inches
h=height—inches The volume compliance, $C_{volume}$, of accumulator assembly 30 is:

$$C_{volume} = \frac{A_D^2}{K_e} - \text{in.}^3/\text{psi} \quad \text{Eq. 3}$$

Infinite compliance for small changes in liquid volume is obtained when $K_e$=0. By setting $K_e$=0 in Eq. 1 and solving for H we obtain:

$$H = \frac{L \pm \sqrt{L^2 - 4m}}{2} \quad \text{Eq. 4}$$

$$\text{where } m = \frac{L}{F_M}(K_D C^2 + K_A B^2 + T_p + K_M A^2) \quad \text{Ew. 5}$$

Eq. 4 provides two solutions for H. Each positive, real solution is valid and may be used. Where two valid solutions exist that smaller H is preferred since it results in a more compact liquid supply assembly 32.

The liquid supply pressure, $P_s$, in accumulator assembly 30 is:

$$P_s = \frac{F_M \frac{A}{C} + F_A \frac{B}{C} + F_D + \frac{(T_p \times \text{change in a})}{C}}{A_D} - \text{psi} \quad \text{Eq. 6}$$

Normally diaphragm 54 and flexure pivot 44 are undeflected from their relaxed positions and thus $F_D$ and change in a are nearly zero and may usually be neglected. Eq. 6 then becomes:

$$P_s = \frac{F_M \frac{A}{C} + F_A \frac{B}{C}}{A_D} - \text{psi} \quad \text{Eq. 7}$$

$F_M$ is set to give the desired minimum value of $P_s$ when $F_A$ is zero. H is calculated from this value of $F_M$ using Eqs. 4 and 5. Then $F_A$ is calculated to give the maximum value of $P_s$.

$F_A$ is adjusted by varying the extension of adjustment spring 70 by linear motion produced by adjustment actuator 18 which moves one end of adjustment spring 70 through coupling 76. The other end of adjustment spring 70 is supported at a location opposite Pivot P so that negligible changes in moment arm B occur with small changes in angle a. Thus there is no significant change in total spring rate $K_e$ as $F_A$ is varied from minimum to maximum. The spring rate of adjustment spring 70 is chosen so the desired adjustment range of $P_s$ can be obtained with the available linear motion of adjustment actuator 18. For the preferred embodiment the available motion is about 0.500 inch with 0.001 inch per step of the stepping motor. For an adjustment range of 0–50% of $P_s$ each step therefore produces about 0.1% change in $P_s$. This provides fine control of $P_s$ setting.

When used with flow cytometer 12 the liquid supply system 10 is usually operated so as to increase $P_s$ as liquid temperature entering the flow cytometer 12 decreases to compensate for the effects of increased liquid viscosity and thus maintain constant both liquid flow and velocity through flow cytometer 12. Constant liquid velocity allows for fixed settings for delay time in drop-in-air and catcher tube sorters as well as the transit time for cells passing between laser beams in a cell analyzer. Liquid temperature sensor 14 provides a signal to adjustment control 16 which then sends the appropriate number of electrical step signals to adjustment actuator 18 to drive it from a home or fixed starting position to the desired compensated operating position and thus apply the required extension to adjustment spring 70 to obtain the required supply pressure $P_s$. Adjustment control 16 may use an EPROM or other suitable memory device to accomplish the function of a look-up table of stepper motor steps versus fluid temperature. The adjustment control 16 has conventional electronics suitable for driving the stepper motor of the adjustment actuator 18. The adjustment control 16 may be implemented in various ways by those skilled in the art and is therefore not described in more detail here.

While the adjustment control 16 is shown as responsive to liquid temperature it is obvious that it could be responsive to any suitable operating parameter of flow cytometer 12 which can be sensed to provide either a closed loop control of that parameter or a programmed bias of $P_s$ produced in response to that parameter. Such parameters may be, for example, liquid flow as sensed by the transit time for a particle to pass through two laser beams or particle velocity as sensed by the time duration of a signal produced by a particle passing through the analysis region. A liquid flow parameter may also be sensed by the pressure drop across an orifice through which the liquid flows.

When such programmed or automatic control of $P_s$ is not required, $P_s$ may be adjusted by the apparatus shown in FIG. 4. The manual adjustment 104 is supported by support plate 102 and is threadably engaged with manual adjustment coupling 106 which is prevented from rotating by having a square cross-section slidably engaged in a square hole in main support 40. As manual adjustment 104 is rotated, manual adjustment coupling 106 moves linearly to change the extension of adjustment spring 70. This changes its force, $F_A$, which in turn changes $P_s$ as set forth in Eq. 7. With a 32 thread per inch thread and a 50% change in $P_s$ with a 0.500 inch motion of manual adjustment coupling 106, there is about a 3% change in $P_s$ for each revolution of manual adjustment 104.

In conclusion, it can be readily understood that liquid supply system 10, constructed according to the teachings of the invention provides a simple, compact, and economical apparatus for providing pulse-free pressurized liquid having no additional dissolved air at a pressure which is independent of liquid level in the supply reservoir, wherein this pressure may be adjusted manually or automatically to compensate for liquid temperature changes to provide for constant liquid flow and constant velocity or particles passing through a flow cytometer analysis and/or sorting region (s).

While the above description contains many specifications, these should not be construed as limitations on the scope of the invention, but rather as an example of one preferred embodiment of the invention. Many other variations are possible without departing from the teachings of the invention, of which a few alternatives will now be described:

The diaphragm pump 22 could be replaced by a peristaltic tubing pump or any other pump with suitable characteristics. The volume sensor 28 could be replaced with any non-contact proximity sensor such as for instance eddy current or capacitive devices. The accumulator 30 could use an unconvoluted or flat diaphragm. The adjustment actuator 18 could be replaced by any suitable electromechanical device such as for instance a rotary stepper motor driving a pinion gear coupled to a gear rack. It is also felt that adjustment actuator 18, liquid temperature sensor 14, and adjustment control 16 could be replaced by a non-electric means for adjustment of liquid pressure such as for instance a liquid thermal expansion apparatus. A sealed stainless steel bellows containing a liquid possessing a high thermal volume expansion characteristic could be placed in and exposed to the liquid passing through the accumulator body. One end of the bellows would be disposed in contact with the accumulator body. The other end of the bellows would be disposed so as to contact a compression spring interposed between the bellows and the accumulator diaphragm. In operation, as liquid temperature increases the liquid in the bellows expands, the bellows extends, the spring is further compressed, and the increased force on the diaphragm produces a decreased regulated fluid pressure $P_s$. Flexure pivot 44 may be replaced with any suitable low friction bearing such as a ball bearing. A KNF Neuberger NF30KVDC pump with is rated for 15 psi it is selected for the pump 22 and pump motor 24 combination in the preferred embodiment. For higher pressures a KNF Neuberger NF1.30KVDC pump which is rated for 85 psi continuous operation may be substituted. Both pumps are manufactured by KNF Neuberger, Inc. of Trenton, N.J. Higher regulated liquid pressures may be obtained by the use of a smaller area diaphragm or by higher force main and adjustment springs in accumulator assembly 30 without increasing the size of the liquid supply assembly 32.

I claim:

1. In a liquid delivery system of the type comprising a supply reservoir, a pump, and an outlet useful for supplying from said outlet a liquid under pressure, the improvement wherein there is interposed between said pump and said outlet a) a liquid accumulator means incorporating both pressure regulating means and volume sensing means and b) a control means responsive to said volume sensing means for providing substantially continuous modulation of power to a pump drive means whereby substantially constant and pulse-free liquid pressure is produced over a range of liquid flow from zero up to the maximum capacity of said pump.

2. The liquid delivery system of claim 1 wherein said pump includes at least one pumping diaphragm with inlet and outlet check valves and said pump driving means produces reciprocating motion of said pumping diaphragm.

3. The liquid delivery system of claim 1 wherein said pressure regulating means includes a housing enclosing a flexible diaphragm exposed on one side to said liquid pressure and loaded on the opposite side by an opposing force means whereby small increases in liquid volume within said housing cause said opposing force to either decrease or remain substantially constant.

4. The liquid delivery system of claim 3 wherein said opposing force means includes a pivotably supported sensor lever loaded by force from an extension spring pivotably attached to said sensor lever at a point so located that as said sensor lever executes small movements about said pivot in response to increases in liquid volume in said accumulator, the fractional increase in said spring force is equal to or less than the fractional decrease in the distance from the line of action of said spring force to said pivot, thus producing zero or negative changes in the moment about said pivot thereby producing zero or negative changes respectively in the force on said diaphragm connected to said sensor lever.

5. The liquid delivery system of claim 4 further including an additional spring acting on said sensor lever to increase the liquid pressure wherein said negative changes in force on said diaphragm substantially equal the sum of all positive changes in force on said diaphragm produced by said diaphragm, said pivot, and said additional spring due to small movements about said pivot produced by increases in liquid volume in said liquid accumulator.

6. The liquid delivery system of claim 4 wherein said sensor lever pivot is comprised of a thin sheet of rigid material fastened on one side to a support member and fastened on the opposite side to said sensor lever thus permitting small rotational movements of the sensor lever about a virtual pivot within the elastic limit of said rigid material.

7. The liquid delivery system of claim 1 wherein the liquid accumulator means has a volume compliance as defined by Equations 1, 2 and 3:

$$K_e = K_D + K_A \frac{B^2}{C^2} + \frac{T_p}{C^2} + K_M \frac{A^2}{C^2} - F_M \frac{(L-H)}{L} \frac{H}{C^2} - \text{lb/in.} \quad \text{Eq. 1}$$

$$\text{where } T_p = \frac{Ewt^3}{12h} - \text{inch lbs./radian} \quad \text{Eq. 2}$$

where for pivot support (44):
E=Young=s modulus of elasticity—psi
w=width—inches
t=thickness—inches
h=height—inches $$C_{volume} = \frac{A_D^2}{K_e} - \text{in.}^3/\text{psi} \quad \text{Eq. 3}$$

and wherein the value of H is selected to be equal to the value derived from Equations 4 and 5:

$$H = \frac{L \pm \sqrt{L^2 - 4m}}{2} \quad \text{Eq. 4}$$

$$\text{where } m = \frac{L}{F_M}(K_D C^2 + K_A B^2 + T_p + K_M A^2) \quad \text{Ew. 5}$$

8. The liquid delivery system of claim 7 wherein the value of H is selected to approximate the value derived from Equations 4 and 5.

9. The liquid delivery system of claim 5 wherein said additional spring has the end distal to said sensor lever pivotably attached to to linearly movable means whereby said additional spring force acting on said sensor lever may be adjusted to produce vatiations in said regulated pressure.

10. The liquid delivery system of claim 9 wherein said linearly movable means comprises a knob integral with a threaded member, supported to resist linear motions and to permit rotational motion, engaged with threads in a slidable member supported to resist rotational motion, said slidable member pivotably coupled to said additional spring whereby rotational motion of said knob produces variations in said regulated liquid pressure.

11. The liquid delivery system of claim 9 wherein said linearly movable means comprises a linear electric stepper motor actuator whereby electric voltage pulses extend or retract the output shaft of said actuator with said additional spring pivotably coupled to said output shaft whereby said electric voltage pulses produce variations in said regulated liquid pressure.

12. The liquid delivery system of claim 11 wherein said electric voltage pulses are produced by a control means producing a position of said output shaft predetermined by the liquid temperature at said liquid delivery system outlet.

13. The liquid delivery system of claim 12 wherein said control means comprises a memory device selected from a group consisting of look-up tables and electrically programmable memories where a predetermined number of electrical pulses are defined by said memory device with said liquid temperature as input signal.

14. The liquid delivery system of claim 3 wherein said volume sensing means comprises a device to continuously sense some portion of the displacement of said diaphragm in said pressure regulating means and produce an electrical signal substantially proportional to said displacement and thus sunstantially proportional to liquid volume change producing said diaphragm displacement.

15. The liquid delivery system of claim 14 wherein said device includes a light source means and a light sensing means with said sensor lever interposed therebetween, whereby said sensor lever, being operably connected to said diaphragm, produces changes in light received by said light sensing means proportional to displacement of said diaphragm thereby providing an input signal to said control means.

16. The liquid delivery system of claim 14 wherein said control means comprises amplifying means operably disposed to regulate the power to said pump drive means whereby discharge of said pump is regulated throughout at least 90% of each discharge cycle of said pump and whereby the liquid volume in said pressure regulating means is maintained substantially constant.

* * * * *